United States Patent [19]

Klein et al.

[11] Patent Number: 5,430,166

[45] Date of Patent: Jul. 4, 1995

[54] SILANES WITH HYDROPHILIC GROUPS, THEIR SYNTHESIS AND USE AS SURFACTANTS IN AQUEOUS MEDIA

[75] Inventors: Klaus-Dieter Klein, Mülheim; Wilfried Knott; Götz Koerner, both of Essen, all of Germany

[73] Assignee: Th. Goldschmidt AG, Essen, Germany

[21] Appl. No.: 265,078

[22] Filed: Jun. 24, 1994

[30] Foreign Application Priority Data

Jun. 24, 1993 [DE] Germany .................. 43 20 920.3

[51] Int. Cl.⁶ .................... C07F 7/08; C07F 7/18
[52] U.S. Cl. ........................ 556/428; 556/437;
  556/440; 556/445; 252/351; 252/353
[58] Field of Search ............ 556/428, 437, 440, 445;
  252/351, 353

[56] References Cited

U.S. PATENT DOCUMENTS

| | | | |
|---|---|---|---|
| 2,582,568 | 1/1952 | Speier | 556/440 |
| 2,640,064 | 5/1953 | Speier | 556/440 |
| 2,872,434 | 2/1959 | Barnes | 556/440 |
| 3,109,012 | 10/1963 | Rossmy et al. | 556/428 |
| 3,141,898 | 7/1964 | Tiers | 556/428 |
| 3,161,611 | 12/1964 | Rossmy | 556/428 X |
| 3,729,444 | 4/1973 | Bey et al. | 556/440 X |
| 4,152,165 | 5/1979 | Langager et al. | 556/428 X |
| 4,235,638 | 11/1980 | Beck et al. | 556/428 X |
| 5,326,844 | 7/1994 | Fujiki et al. | 556/440 X |

FOREIGN PATENT DOCUMENTS

| | | |
|---|---|---|
| 0367381 | 5/1990 | European Pat. Off. . |
| 4141046 | 2/1993 | Germany . |
| 1520421 | 8/1978 | United Kingdom . |

OTHER PUBLICATIONS

Die temperaturabhängigkeit der Benetzung, Aug. 12, 1969, 5 pgs, by A. W. Neumann.
Syntheses and Properties of Surfactants . . . , 1970, 7 pgs, Hirohisa Maki, et al.
Syntheses and Properties of Surfactants . . . , 1970, 5 pgs, Hirohisa Maki, et al.

*Primary Examiner*—Paul F. Shaver
*Attorney, Agent, or Firm*—Anderson Kill Olick & Oshinsky

[57] ABSTRACT

Silanes of the general formula

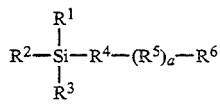

are prepared wherein
  $R^1$, $R^2$ and $R^3$ in the molecule are the same or different and represent aliphatic hydrocarbon groups,
  $R^4$ is a divalent hydrocarbon group with 3 to 14 carbon atoms,
  $R^5$ is a group having the formula $-O(CH_2)_b-$ or a polyether group having the formula $-(OC_nH_{2n})_c-$, wherein b has a value of 1 to 6, n has an average value of 2 to 2.5 and c has a value of 1 to 10,
  $R^6$ is an $-OSO_3X$ group or an $-OR^7$ group, wherein X is a hydrogen, an alkali or an optionally substituted ammonium ion and $R^7$ is an alkyl group with 1 to 4 carbon atoms or an acetyl group,
  a is 0 or 1,
with the proviso that, when $R^6$ represents the $-OR^7$ group, a=1. The silanes are biologically degradable, resistant to hydrolysis and have pronounced surfactant properties.

19 Claims, No Drawings

SILANES WITH HYDROPHILIC GROUPS, THEIR SYNTHESIS AND USE AS SURFACTANTS IN AQUEOUS MEDIA

FIELD OF THE INVENTION

The invention relates to novel silanes with hydrophilic groups, their synthesis and use as surfactants in aqueous media. More particularly, it relates to hydrolysis-resistant silane surfactants, which have the ability to drastically lower the surface tension of aqueous media. The concept of "aqueous" media is understood to include also those media which consist predominantly of water and additionally may contain water-soluble or water-miscible organic solvents.

BACKGROUND INFORMATION AND PRIOR ART

It is known from the state of the art that organo-modified siloxanes, such as polyether siloxanes or polysiloxanes, which have substituents having anionic, cationic or amphoteric groups, an appropriately selected structure and a balanced ratio of hydrophilic to hydrophobic groups, can lower the surface tension of aqueous solutions to a pronounced degree.

Surfactants with at least three silicon atoms are described in the German patent 41 41 046. They correspond to the general formula

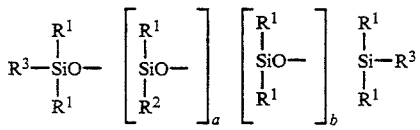

wherein $R^1$ are methyl or phenyl groups, with the proviso that at least 90% of the $R^1$ groups are methyl groups, $R^2$ is identical with $R^1$ or —(CH$_2$)$_6$—SO$_3^-$.M$^+$, wherein M$^+$ is an alkali, ½ an alkali earth or optionally an alkyl-substituted ammonium ion, $R^3$ is identical with $R^1$ or $R^2$ with the proviso that at least one $R^2$ or $R^3$ group in an average molecule is a —(CH$_2$)$_6$—OSO$_3^-$.M$^+$ group, a has a numerical value of 0 to 5, and b has a numerical value of 0 to 5.

In neutral, aqueous media, the selected trisiloxanehexyl sulfates having three silicon atoms bring about a pronounced decrease in the surface tension of the media to values of about 21 mN/m. However, in acidic or alkaline solutions, they are not stable and, due to hydrolysis of the Si-O-Si bonds and renewed condensation of the hydrolysis products to higher molecular weight oligomers, rapidly lose their effectiveness and partly become insoluble in aqueous media.

Surfactants with a low content of silicon atoms are furthermore described in the European publication 0 367 381 (A2) and the British patent 1,520,421.

The European publication 0 367 381 (A2) relates to organosilicon compounds of the general formula

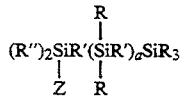

wherein

R independently of one another represent an alkyl, aryl, halogenated alkyl or halogenated aryl group with up to 18 carbon atoms each, R' represents an alkylene group, which separates adjacent silicon atoms from one another by up to 6 carbon atoms, R" independently of one another represent R or, when a is equal to zero, the R$_3$SiR' group, Z is a hydrophilic substituent, which contains sulfur, nitrogen or phosphorus, a carboxy-functional group or its salt, and a has a value of 0, 1 or 2.

It follows from this that the organosilicon group, by definition, contains at least two silicon atoms. The synthesis of these carbosilanes is relatively expensive and is accomplished, for example, by a method similar to a Grignard reaction. After that, carbosilane surfactants, with a quaternary, sulfonate or betaine structure, are synthesized by means of a hydrosilylation of, for example, allyl glycidyl ether or allylamine and well-known subsequent reactions. The substances, so obtained, lower the surface tension of a 1% solution in distilled water to 23 to 25 mN/m.

In the British patent 1,520,421, carbosilane surfactants and their synthesis are described. They have the general formula

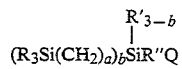

wherein

R is a methyl, ethyl, propyl or trifluoropropyl group, with the proviso that at least 50% of the R groups are methyl groups, R' is an alkyl group with 1 to 6 carbon atoms, R" is a divalent aliphatic hydrocarbon group with 2 to 6 carbon atoms, which connects Q and the adjacent silicon atom by means of a bridge of at least 2 carbon atoms, Q is the —O(C$_2$H$_4$O)$_c$X group, wherein c has a value of 3 to 12 and X is a hydrogen group, R''' is

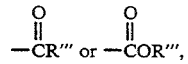

in which R''' is an alkyl group with 1 to 5 carbon atoms and a=1 or 2 and b=2 or 3.

According to the definition, at least two silicon atoms must be present here also. In application tests, these compounds exhibit remarkable foaming properties.

It was known to those skilled in the art that the surfactant properties of the compounds within groups of known carbosilanes with comparable structure deteriorate as the number of silicon atoms decreases, in particular, as the number of silicon atoms is decreased from 4 to 3 or 2. This observation is embodied in the theory of Neumann (A. W. Neumann, D. Renzow, Zeitschrift f. Phys. Chem., new issue 68, 11 (1969), which states that the permethylated surface of the siloxane backbone is responsible for the lowering of the surface tensions of aqueous solutions to values below 30 to 40 mN/m.

Furthermore, reference is made to the Japanese publications of H. Maki et al. in YUKAGAGU 19, No. 4, page 51 ff. and YUKAGAGU 19 No. 11, page 23 ff., both from 1970, wherein defined compounds of the formula (CH$_3$)$_3$Si(CH$_2$)$_3$(C$_2$H$_4$O)$_n$H and
((CH$_2$)$_4$)$_3$Si(CH$_2$)$_3$(C$_2$H$_4$O)$_m$H are described, in which n=4.0 or 7.7 and m=10 or 17. However, these compounds lower the surface tension of a 1% by weight solution only to values not less than 26.5 mN/m.

In these Japanese publications, quaternary nitrogen compounds of the formula

Bu$_3$M(CH$_2$)$_3$N$^+$(CH$_3$)$_3$Cl$^-$ (Bu=Butyl, M=Sn, Si)

are also described. Admittedly, these compounds have bacteriostatic activity; however, they are not very surface active. The best representatives of these quaternary compounds bring about a surface tension lowering to 32 mN/m in a 1% aqueous solution.

The present invention is based on the surprising finding that, in contrast to general theoretical knowledge, as expressed, for example, in the theory of Neumann, selected silanes, that is, compounds with only a single silicon atom, for which the ratio of hydrophilic to hydrophobic parts of the molecule is balanced, lower the surface tension of water extraordinarily effectively and, in contrast to the siloxane surfactants, are resistant to hydrolysis for days and weeks, even in acidic and alkaline media. A further and unforeseeable advantage of the inventive silanes is their complete biological degradability, which makes them particularly suitable for use as surfactants. Such a profile of properties could not be inferred from the state of the art and contradicts previously customary assumptions concerning the structural requirements, which organosilicon compounds should meet in order to exhibit surface tension-lowering properties in aqueous systems.

OBJECT OF THE INVENTION

An object of the present invention are inventive silanes. Another object of the invention is the synthesis of the inventive silanes. Yet another object of the invention is a method of reducing surface tension of aqueous media by adding the inventive silanes. A further object of the invention is an aqueous solution containing 1% by weight of silanes whereby surface tension of the solution is reduced.

The inventive silanes are of the general formula

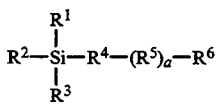

wherein
R$^1$, R$^2$ and R$^3$ in the molecule are the same or different and represent aliphatic hydrocarbon groups,
R$^4$ is a divalent hydrocarbon group with 3 to 14 carbon atoms,
R$^5$ is a group having the formula —O(CH$_2$)$_b$— or a polyether group having the formula —(OC$_n$H$_{2n}$)$_c$—, wherein b has a value of 1 to 6, n has an average value of 2 to 2.5 and c has a value of 1 to 10,
R$^6$ is an —OSO$_3$X group or an —OR$^7$ group, wherein X is a hydrogen, an alkali or an optionally substituted ammonium ion and R$^7$ is an alkyl group with 1 to 4 carbon atoms or an acetyl group, and a is 0 or 1,
with the proviso that, when R$^6$ represents the —OR$^7$ group, a=1.

SUMMARY OF THE INVENTION

Examples of preferred R$^1$, R$^2$ and R$^3$ groups are methyl, ethyl, propyl or butyl groups.

Preferably, at least 90% of the R$^1$, R$^2$ and R$^3$ groups are methyl groups.

R$^4$ is a divalent hydrocarbon group with 3 to 14 carbon atoms, such as —C$_3$H$_6$—, —C$_5$H$_{10}$ , C$_6$H$_{12}$— or C$_{11}$H$_{22}$— groups. The R$^4$ groups can be substituted, for example, by lateral alkyl groups or halogen groups. However, linear hydrocarbon groups are preferred.

Further examples of R$^4$ groups are groups of the formula

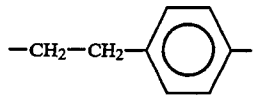

and

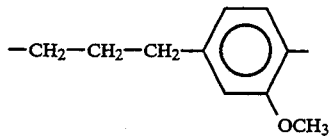

Preferably, R$^4$ is a divalent, aliphatic hydrocarbon group with 3 to 9 carbon atoms, particularly with 3 to 6 carbon atoms.

R$^5$ is a group having the formula —O(CH$_2$)$_b$— or a polyether group having the formula —(OC$_n$H$_{2n}$)$_c$—, wherein b has a value of 1 to 6, n has an average value of 2 to 2.5 and c has a value of 1 to 10. Examples of such groups are the —O(CH$_2$)$_4$—, —(OC$_2$H$_4$)$_c$— or —(OCH(CH$_3$)CH$_2$)$_c$— groups.

n preferably has a value of 2.0, so that, in this case, all oxyalkylene units are oxyethylene units. The subscript c indicates the number of these units and has a value of 1 to 10 and preferably of 3 to 6.

R$^6$ is an —OSO$_3$X group or an —OR$^7$ group, wherein X is a hydrogen, an alkali or an optionally substituted ammonium ion and R$^7$ is an alkyl group with 1 to 4 carbon atoms or an acetyl group. As substituted ammonium ions, particularly isopropyl, triethyl, butylmethyl or octylammonium ions come into consideration. When R$^7$ is an alkyl group, the methyl, ethyl or propyl group is preferred.

a has a value of 0 or 1.

The proviso that a=1 when R$^6$ represents the —OR$^7$ group ensures that the following types of inventive silanes are included:

a) silanes, which have a spacer group, to which a terminal sulfato group is linked directly,
b) silanes, which have a spacer group, to which a polyether group is linked, to which, in turn, a sulfato group is linked terminally, and
c) silanes, which have a spacer group, to which a polyether group is linked, which, in turn, has a terminal OR$^7$ group.

Examples of inventive silanes are

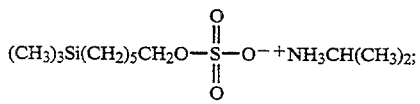

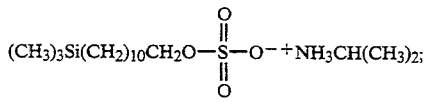

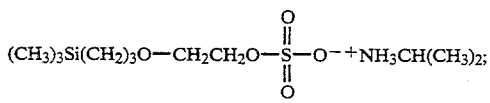

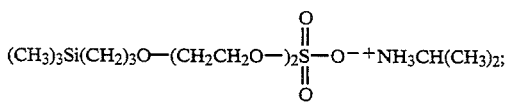

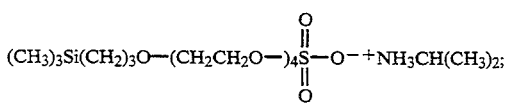

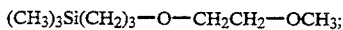

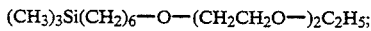

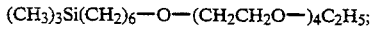

and

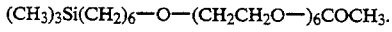

The inventive compounds can be synthesized by different methods, which are characterized in that
a) either
(i) compounds of the general formula $CH_2=CH-R^8-OH$, in which $R^8$ is a divalent aliphatic hydrocarbon group with 1 to 12 carbon atoms, are added in the presence of a hydrosilylation catalyst and optionally c moles of an alkylene oxide of the general formula

are added in the presence of an alkaline catalyst or a Lewis acid, or
(ii) compounds of the general formula $CH_2=CH-R^8-(R^5)_a-OH$, in which $R^5$ and $R^6$ have the meanings already given, are added in the presence of a hydrosilylation catalyst, or
(iii) compounds of the general formula $CH_2=CH-R^8-(R^5)_a-OR^7$, in which $R^5$, $R^7$ and $R^8$ have the meanings already given
are added in an addition reaction to silanes of the general formula

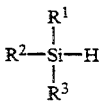

and
b) the compounds, which are obtained by methods (i) and (ii) and have the formula

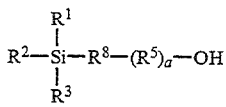

are sulfated in a known manner and, if desired, neutralized with alkali hydroxide or ammonium hydroxide, the hydrogen atoms on the nitrogen may be substituted.

Preferably, the hydrosilylation reaction is carried out at an elevated temperature and/or in the presence of a solvent, a platinum catalyst being used as catalyst.

For variation (i) of the method, an alcohol, which has a terminal olefinic double bond, is initially reacted in an addition reaction with the SiH silane. To the terminal OH group of the hydrosilylation product obtained, c moles of an alkylene oxide or alkylene oxide mixture are added in the presence of a known alkoxylation catalyst. As alkoxylation catalysts, alkaline catalysts, such as potassium hydroxide, sodium hydroxide, alkali alcoholates or Lewis acids, such as $BF_3$-etherate preferably are used. The polyether monool obtained is subsequently sulfated in a known manner and optionally neutralized with alkali hydroxide or with ammonium hydroxide that can be substituted with hydrocarbon groups at the nitrogen atom. The ammonium salt, formed during the reaction, can also easily be converted into the corresponding alkylammonium salt by a metathesis reaction with alkylamines, ammonia being split off. The properties of the sulfate ester salts obtained can be modified by using appropriate alkylamines. This refers particularly to the wetting foaming capabilities.

It is known to those skilled in the art that the critical micelle concentration (cmc) in aqueous solutions, which is an important parameter for characterizing the surfactant behavior of a compound, depends on the degree of bonding of the counterion to the rest of the surfactant. For example, the cmc of the surfactant decreases as the counter ion is bound more strongly to the rest of the surfactant. The degree of bonding depends on the polarizability, the valence and the hydrate shell of the counterion. The specific surfactant properties, such as the foaming and wetting capabilities, the solubility and the surface tension lowering effect of a compound are therefore affected not only by the surfactant group, but also by the counterion. Accordingly, it is also understandable that, in view of the plurality of organic ammonium cations that are available and the technically very simple conversion of the compound claimed into the corresponding alkylammonium derivatives, a plurality of compounds with valuable application properties can, of course, also be synthesized.

For the second variation (ii) of the method, the already alkoxylated alcohol, which has a terminal double bond, is added in an addition reaction to the hydrogensilane and can then, as described above, be sulfated and neutralized.

For a third variation (III) of the method, the olefinically unsaturated compound $CH_2=CH-R^8-(R^5)_a-OR^7$ is added in an addition reaction to the SiH silane. Even though reactions at the terminal $OR^7$ groups are possible, the reaction product is used mostly in the form so obtained.

For optimizing the interfacial properties of the inventive compounds, their hydrophilic and hydrophobic properties must be present in a balanced ratio. The hydrophobic properties can be affected by way of the $R^1$, $R^2$, $R^3$ and $R^7$ groups. The higher the carbon content of these groups, the more hydrophobic is the inventive silane. The hydrophilicity is determined, in particular, by the $R^5$ group and the anionic sulfate group. The lower the numerical value of n within the given range and the higher the numerical value of c, the more hydrophilic is the silane surfactant. This effect on the surfactant properties is explained in greater detail in the Examples and thus becomes easily understandable to those skilled in the art. Only a few reasonable preliminary experiments, which do not involve any inventive effort, are required for achieving the desired properties.

A further object of the invention is the use of the inventive silanes as surfactants in aqueous media. In this connection, it is possible to reduce the surface tension of aqueous solutions to values of about 21 mN/m by the addition of 1% by weight of the inventive compounds. Moreover, the biological degradability of the inventive compounds is of quite special importance. It is supplemented by the resistance of the silane surfactants to hydrolysis.

Important, possible uses for the inventive silane surfactants are, for example:

as wetting agents:
  in preparations for the treatment of plants (agricultural formulations); to improve the wetting of substrates with a low surface free energy, such as polyethylene or polypropylene surfaces; for use in the paint industry; for the production of photographic films; in electroplating;

as dispersant:
  for dispersions paints, pigments and fillers; as emulsifiers or additives in the textile industry for the preparation of textile auxiliaries, softeners, lubricants, antistatic preparations; as dyeing aids;

as surfactants in general:
  for use in fire extinguishers; as foam stabilizers, as surface active additives for high-speed printing inks, adhesives, dispersion adhesives, melt adhesives, use in detergents; as additives for industrial cleaners;

as raw material for use in cosmetics, shampoos, shower gels; and in technical applications and in the house:
  as anti-fogging aid; for use in dish-washing detergents, detergents, toilet cleaners, automatic gloss emulsions.

The synthesis of the inventive compounds and their properties are described in even greater detail in the following Examples, it being understood that the Examples are provided by way of illustration and not by way of limitation.

EXAMPLE 1 a) Synthesis of 6-Hydroxyhexyltrimethylsilane (not of the invention)

1-Hexene-5-ol (28.7 g, 0.287 moles) and 3 mg of platinum catalyst are weighed into a 300 mL laboratory autoclave. Under an argon blanket, the autoclave with contents is now cooled in an acetone/dry ice bath and 22.4 g of trimethylsilane (0.299 moles with a boiling point of 6.7° C.) are siphoned over from the condensed phase. The autoclave is closed and heated to 130° C. At the same time, the internal pressure increases to 13.7 bar, only to drop once again then to about 5.7 bar. This drop in pressure indicates a reaction.

After the pressure in the autoclave has been relieved, which is done after the autoclave has been cooled to room temperature, the contents are freed from the platinum catalyst by filtration (weight: 50.7 g, mass loss: 0.9 g). Hydroxyl number—theoretical: 321.7; actual: 306.0.

$^{29}$Si-NMR and $^1$H-NMR analysis reveal the structure of the product to be as follows:

$(CH_3)_3Si(CH_2)_6OH$

The product is freed from highly volatile components at 20° C. under the vacuum of an oil pump.

b) Synthesis of a Polyoxyethylenetrimethylsilane by the ethoxylation of hydroxyhexyltrimethylsilane (not of the invention)

Hydroxyhexyltrimethylsilane (20.0 g, 0.11 moles) and 0.82 g of a 50% boron trifluoride solution in ether are added to a 3-neck flask, which is equipped with an intensive condenser, thermometer, dropping funnel equipped with cooling mantle and a nitrogen connection. Condensed ethylene oxide (21.1 g, 0.48 moles) is then slowly added dropwise. The exothermic reaction is counteracted with an ice bath, so that the internal temperature does not exceed 20° to 30° C. After that, stirring is continued for two hours at room temperature. After neutralization with 1.50 g of sodium hydrogen carbonate and 0.41 g of water (1% by weight) the volatile components are removed from the product at 90° C. under the vacuum of a water jet pump. The subsequent filtration with prior addition of filter aids results in a weakly yellow, clear product which, according to $^1$H spectroscopy as well as gel permeation chromatography, has 4.2 oxyalkylene units and accordingly can be reproduced by the following average formula:

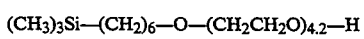

$(CH_3)_3Si—(CH_2)_6—O—(CH_2CH_2O)_{4.2}—H$ c1) Synthesis of an inventive product having the formula

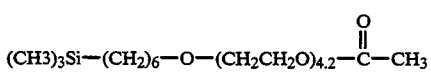

$$(CH_3)_3Si—(CH_2)_6—O—(CH_2CH_2O)_{4.2}—\overset{\overset{O}{\|}}{C}—CH_3$$

To a 3-neck flask, equipped with reflux condenser and an internal thermometer, 31.45 g (0.087 moles) of the product 1b), 14 g (0.3 moles) of acetic anhydride, 1.9 g of sodium acetate and 100 mL of toluene are added and heated under reflux for 2 hours.

After the solvent is distilled off, the acid number is 9.7. Sodium hydrogen carbonate, suspended in a little water, is added to the crude product in order to neutralize it.

After that, the volatile components are removed at about 90° C. under the vacuum of a water jet pump and the precipitated salts are filtered off.

This product is dissolved in distilled water to form a 1 or 0.1% by weight solution. After standing for 24 hours, these solutions are investigated for their spreadability on a polypropylene sheet (50 μL drops).

TABLE 1

| Concentration (% by weight) | Spreading (mm) Polypropylene Sheet |
|---|---|
| 1.0 | 20 |
| 0.1 | 10 | c2) Synthesis of an Inventive Product having the Formula $(CH_3)_3Si—(CH_2)_6—O—(CH_2CH_2O)_{4.2}—CH_3$ To a 3-neck flask, equipped with reflux condenser, stillhead and internal thermometer, 37.5 g (0.1 moles) of product 1b) are added and slowly mixed at 115° C. with 27 g of sodium methanolate solution (0.15 moles, 30% in methanol). The methanol formed is distilled off continuously by applying a slight vacuum.

At the end of the addition, the remaining methanol is removed, at first under the vacuum of a water-jet pump and then under the vacuum of an oil pump. Subsequently, the apparatus is filled with nitrogen and methylene chloride is passed in rapidly with vigorous stirring. The internal temperature is kept below 120° C. by means of an ice bath. When it is noted that the exothermic reaction has abated, the temperature can be maintained at 115° to 120° by external heating.

After hardly any alkali can be detected in the reaction batch by determining the alkali number, the addition of methylene chloride is ended. After the reaction mixture is cooled to 60° C., 2 mL of water are added and the batch is neutralized with 30% aqueous phosphoric acid solution. The crude product is freed from volatile components at 60° C. in a rotary evaporator under the vacuum of a vacuum pump and, after the addition of filter aids, is filtered.

A yellowish, clear product is obtained, which dissolves in water to form a cloudy solution. Aqueous solutions of this product show the following, concentration-dependent surfactant properties:

TABLE 2

| Concentration (% by weight) | Spreading (mm) Polypropylene Sheet |
|---|---|
| 1.0 | 50 |
| 0.1 | 30 |

EXAMPLE 2 a) Synthesis of a polyoxyalkylenetrimethylsilane having the formula $(CH_3)_3Si(CH_2)_6(OCH_2CH_2)_4OH$ by Hydrosilylation (intermediate, not of the invention)

To a 300 mL laboratory autoclave are added 88.14 g of hexenyl polyether having the formula $CH_2=CH(CH_2)_4(OCH_2CH_2)_4OH$ (0.3 moles with an hydroxyl number of 203.4 and an iodine number of 86.4) and 5 g of platinum catalyst. The autoclave and the contents, in a protective atmosphere of argon, are cooled in an acetone/dry ice bath and 23.34 g of trimethylsilane (0.315 moles) are siphoned over. The autoclave is closed and heated to 130° C. At the same time, the internal pressure increases to 8.0 bar, only to drop then once again to about 3.5 bar.

After the autoclave is cooled to room temperature and the pressure is relieved, the contents, weighing 109.0 g and thus indicating a mass loss of 0.6 g, are freed from the platinum catalyst by filtration.

Hydroxyl number—theoretical: 152.5; actual: 158.0.

A water-white product of low viscosity is obtained, which dissolves in water to form a cloudy, 1% solution.

b) Synthesis of (Isopropylammonium-6-Sulfatohexyl)-trimethylsilane by Sulfating with Amidosulfuric Acid (of the invention)

In a 100 mL 4-neck flask, equipped with stirrer, reflux condenser, thermometer and dropping funnel, 18.33 g of (hydroxyhexyl)trimethylsilane (0.1 moles, a product of Example 1), 10.19 g of freshly pestled amidosulfuric acid (0.105 moles) and 9.6 g of dimethylformamide are mixed under an atmosphere of nitrogen and heated for 4 hours at an internal temperature of 85° C. Thereafter, the reaction mixture is mixed at room temperature with 7.09 g of isopropylamine (0.12 moles), the mixture becoming warm and ammonia escaping. By these means, any acid residues present in the product are neutralized at the same time. After that, the product is filtered and freed from N,N-dimethylformamide and excess isopropylamine by being heated to a temperature of 85° C. in the vacuum of an oil pump. A yellowish, transparent product of low viscosity is obtained, which dissolves in water to form a clear solution and then foams greatly when shaken. The 1% solution in distilled water has a surface tension of 21.0 mN/m and spreads to the extent of 55 mm on a polypropylene plate. Analytical examinations by means of $^1$H-NMR and $^{13}$C-NMR spectroscopy confirm that the reaction product has the anticipated structure

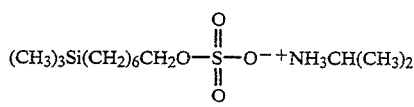

TABLE 3

| Reduction in the Surface Tension as a Function of the Concentration of an Aqueous Solution | |
|---|---|
| Concentration (% by weight) | Surface Tension (mN/m) at 25° C. |
| 1.0 | 20.9 |
| 0.4 | 21.0 |
| 0.3 | 22.5 |
| 0.15 | 25.1 |
| 0.09 | 27.3 |
| 0.07 | 27.9 |

EXAMPLE 3

Synthesis of Further Inventive Compounds and Determination of Their Surfactant Properties Hydroxy-functional trimethylsilane derivatives are synthesized, as shown in the preceding Examples, as further starting materials by the platinum-catalyzed addition reaction of allyl alcohol, 3-butene-1-ol, undecene-1-ol and olefin-functional ethers or polyethers with trimethylsilane. These compounds are subsequently sulfated with amidosulfuric acid and converted into the corresponding ammonium salts.

To begin with, aqueous, 1% by weight solutions of the products are prepared and their surface tensions are determined by the Du Noüy method. To determine the wetting capability, the spreading of a 50 μL droplet of the 1% surfactant solution on a polypropylene sheet is measured over the maximum extent of the area. Under these conditions, pure water gives a blank value of 8 mm. The long-term resistance to hydrolysis is also followed by observing the wetting properties of a 1% solution.

TABLE 4

| Product | Solution | Surface Tension (mN/m) | Spreading (mm) in Polypropylene Film |
|---|---|---|---|
| TMS-C$_3$-SO$_4$ | cloudy | 28.4 | 8 |
| TMS-C$_4$-SO$_4$ | cloudy | 26.5 | 8 |
| TMS-C$_6$-SO$_4$ | clear | 21.0 | 55 |
| TMS-C$_{11}$-SO$_4$ | cloudy | 24.2 | 15 |
| TMS-PE-SO$_4$* | clear | 32.7 | 8 |
| TMS-PE-SO$_4$** | clear | 25.0 | 15 |

TABLE 4-continued

| Product | Solution | Surface Tension (mN/m) | Spreading (mm) in Polypropylene Film |
|---|---|---|---|
| TMS-EO-SO$_4$ | clear | 24.7 | 17 |

TMS-PE-SO$_4$* = TMS-C$_6$-O-(C$_2$H$_4$O)$_4$SO$_3^-$X$^+$
TMS-PE-SO$_4$** = TMS-C$_3$-O-(C$_2$H$_4$O)$_2$SO$_3^-$X$^+$
TMS-EO-SO$_4$ = TMS-C$_3$-O-CH$_2$CH$_2$OSO$^-$X$^-$
TMS = *trimethylsilyl group*
PE = *polyether group*
X$^+$ = isopropylammonium ion The compounds have pronounced surface active properties. In the case of the sulfate esters, the best surface active properties are shown by (isopropylammonium-6-sulfatohexyl)trimethylsilane. When the R$^1$, R$^2$ and R$^3$ groups are identical, it can be seen that the surfactant properties depend on the length of the R$^4$ spacer group. Within a homologous series with 3 to 11 carbon atoms, the properties are optimum when the spacer group has about 6 carbon atoms.

EXAMPLE 4

In a way similar to that described in Example 2, the ammonium salt of trimethylsilylhexyl sulfate can be converted with various organic amine bases into the corresponding alkylammonium salts with release of ammonia. By means of this modification step, products with diverse properties in relation to a surface tension reduction, wetting properties and foaming properties become accessible. This is shown by the following Table.

TABLE 5

| Counterion | Surface Tension 1% by weight in H$_2$O (mN/m) | Spreading 1% by weight in H$_2$O Polypropylene Sheet (mm) | Foam Height 1% by weight in H$_2$O after | | |
|---|---|---|---|---|---|
| | | | 30 s | 180 s | 300 s |
| NH$_4^+$ | 21.7 | 60 | 215 | 175 | 95 |
| (iPr)NH$_3^+$ | 21.0 | 55 | 245 | 180 | 100 |
| (C$_8$H$_{17}$)NH$_3^+$ | 21.6 | 54 | 15 | 12 | 3 |
| (C$_4$H$_9$)NH$_2^+$ | 23.3 | 50 | 250 | 225 | 185 |
| |CH$_3$ | | | | | |
| (C$_2$H$_5$)$_3$NH$^+$ | 21.9 | 58 | 195 | 140 | 45 |

EXAMPLE 5

Checking the Resistance to Hydrolysis of the Inventive Substances at pH 4, pH 7 and pH 12

The wetting behavior of a 1% by weight aqueous solution of (isopropylammonium-6-sulfatohexyl)trimethylsilane as a function of time is demonstrated using the sulfate esters as example.

TABLE 6

| Storage at room temperature (days) | Spreading (mm) at | | | Appearance of the Solution |
|---|---|---|---|---|
| | pH 4 | pH 7 | pH 12 | |
| 0 | 55 | 55 | 45 | clear |
| 1 | 50 | 55 | 40 | clear |
| 2 | 55 | 55 | 45 | clear |
| 3 | 55 | 55 | 50 | clear |
| 4 | 50 | 55 | 45 | clear |
| 7 | 55 | 55 | 45 | clear |
| 8 | 55 | 45 | 45 | clear |
| 9 | 50 | 50 | 45 | clear |
| 10 | 50 | 50 | 45 | clear |
| 70 | 55 | 55 | 50 | clear |

TABLE 6-continued

| Storage at room temperature (days) | Spreading (mm) at | | | Appearance of the Solution |
|---|---|---|---|---|
| | pH 4 | pH 7 | pH 12 | |
| 74 | 60 | 55 | 55 | clear |
| 80 | 65 | 60 | 60 | clear |

The investigation confirms the excellent resistance to hydrolysis in neutral, as well as in alkaline and acidic pH ranges.

COMPARISON EXAMPLE

For comparison, the 1% by weight aqueous solution of a siloxane sulfate ester, which is not of the invention and has the average formula

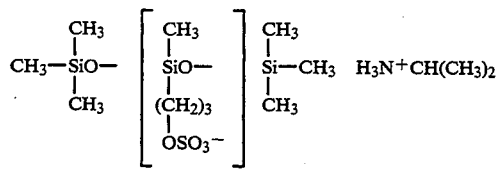

is investigated to determine the stability of the siloxane surfactant in aqueous solutions of different pH.

TABLE 7

| Storage at room temperature (days) | Comparison | | | |
|---|---|---|---|---|
| | Spreading (mm) at | | | Appearance of the Solution |
| | pH 4 | pH 7 | pH 12 | |
| 0 | 48 | 30 | 35 | cloudy |
| 1 | n.o. | 38 | 20 | cloudy |
| 2 | n.o. | 40 | 10 | cloudy |
| 3 | n.o. | 40 | 10 | cloudy |
| 4 | n.o. | 40 | n.o. | cloudy |
| 7 | n.o. | 30 | n.o. | cloudy |
| ≧14 | n.o. | n.o. | n.o. | cloudy | n.o. means that spreading could not be observed and therefore was not measurable.

We claim:
1. Silanes of the general formula

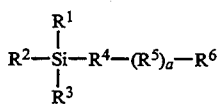

wherein
R$^1$, R$^2$ and R$^3$ in a molecule are the same or different and represent aliphatic hydrocarbon groups,
R$^4$ is a divalent hydrocarbon group with 3 to 14 carbon atoms,
R$^5$ is a group having the formula —O(CH$_2$)$_b$— or a polyether group having the formula —(OC$_n$H$_{2n}$)$_c$—, wherein b has a value of 1 to 6, n has an average value of 2 to 2.5 and c has a value of 1 to 10,
R$^6$ is an —OSO$_3$X group or an —OR$^7$ group, wherein X is a hydrogen, an alkali or an optionally substituted ammonium ion and R$^7$ is an alkyl group with 1 to 4 carbon atoms or an acetyl group,
a is 0 or 1,
with the proviso that, when R$^6$ represents the —OR$^7$ group, a=1.
2. The silanes of claim 1 further comprising that R$^1$, R$^2$ and R$^3$ are alkyl groups with 1 to 4 carbon atoms.

3. The silanes of claim 2, further comprising that at least 90% of $R^1$, $R^2$ and $R^3$ groups are methyl.

4. The silanes of claims 1 or 2, further comprising that the $R^4$ group is a divalent aliphatic hydrocarbon group with 3 to 14 carbon atoms.

5. The silanes of claim 4, further comprising that the $R^4$ group is a divalent aliphatic hydrocarbon group with 3 to 9 carbon atoms.

6. The silanes of claim 5, further comprising that the $R^4$ group is a divalent aliphatic hydrocarbon group with 3 to 6 carbon atoms.

7. The silanes of claims 1 or 2, further comprising that the $R^5$ group is a polyether group, in which n has a value of 2 and c a value of 3 to 6.

8. The silanes of claims 1 or 2, further comprising that X is an alkylammonium group having alkyl group with 1 to 10 carbon atoms.

9. A method for the synthesis of silanes of the general formula

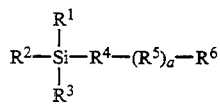

wherein
$R^1$, $R^2$ and $R^3$ in a molecule are the same or different and represent aliphatic hydrocarbon groups,
$R^4$ is a divalent hydrocarbon group with 3 to 14 carbon atoms,
$R^5$ is a group having the formula $-O(CH_2)_b-$ or a polyether group having the formula $-(OC_nH_{2n})_c-$, wherein b has a value of 1 to 6, n has an average value of 2 to 2.5 and c has a value of 1 to 10,
$R^6$ is an $-OSO_3X$ group or an $-OR^7$ group, wherein X is a hydrogen, an alkali or an optionally substituted ammonium ion and $R^7$ is an alkyl group with 1 to 4 carbon atoms or an acetyl group,
a is 0 or 1,
with the proviso that, when $R^6$ represents the $-OR^7$ group, a=1, comprising the steps of:
a) adding, either
(i) compounds of the general formula $CH_2=CH-R^8-OH$, in which $R^8$ is a divalent aliphatic hydrocarbon group with 1 to 12 carbon atoms, in presence of a hydrosilylation catalyst and optionally c moles of an alkylene oxide of the general formula

in presence of an alkaline catalyst or a Lewis acid, or
(ii) compounds of the general formula $CH_2=CH-R^8-(R^5)_a-OH$, in which $R^5$ and $R^6$ have the meanings already given, in presence of a hydrosilylation catalyst, or
(iii) compounds of the general formula $CH_2=CH-R^8-(R^5)_a-OR^7$, in which $R^5$, $R^7$ and $R^8$ have the meanings already given
in an addition reaction to silanes of the general formula

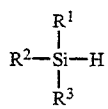

and
b) sulfating the compounds obtained by methods (i) and (ii) above and having the formula

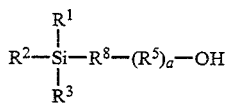

and, if necessary, neutralizing with alkali hydroxide or ammonium hydroxide, and substituting the hydrogen atoms on the nitrogen.

10. The method of claim 9, further comprising that the hydrosilylation is carried out at an elevated temperature or in the presence of a solvent or both.

11. The method of claims 9 or 10, further comprising that the hydrosilylation is carried out in presence of a platinum catalyst.

12. The method of claim 9, further comprising that $R^1$, $R^2$ and $R^3$ are alkyl groups with 1 to 4 carbon atoms.

13. The method of claim 9, further comprising that at least 90% of $R^1$, $R^2$ and $R^3$ are methyl.

14. The method of claim 9, further comprising that the $R^4$ group is a divalent hydrocarbon group with 3 to 14 carbon atoms.

15. The method of claim 9, further comprising that the $R^5$ group is a polyether group, in which n has a value of 2 and c a value of 3 to 6.

16. The method of claim 9, further comprising that X is an alkylammonium group having alkyl group with 1 to 10 carbon atoms.

17. A method of reducing the surface tension of aqueous media comprising adding an effective amount of silanes of the general formula

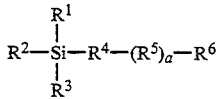

wherein
$R^1R^2$ and $R^3$ in a molecule are the same or different and represent aliphatic hydrocarbon groups,
$R^4$ is a divalent hydrocarbon group with 3 to 14 carbon atoms,
$R^5$ is a group having the formula $-O(CH_2)_b-$ or a polyether group having the formula $-(OC_nH_{2n})_c-$, wherein b has a value of 1 to 6, n has an average value of 2 to 2.5 and c has a value of 1 to 10,
$R^6$ is an $-OSO_3X$ group or an $-OR^7$ group, wherein X is a hydrogen, an alkali or an optionally substituted ammonium ion and $R^7$ is an alkyl group with 1 to 4 carbon atoms or an acetyl group,
a is 0 or 1,
with the proviso that, when $R^6$ represents the $-OR^7$ group, a=1,
as a hydrolysis-resistant surfactant.

18. An aqueous solution containing 1% by weight of silanes of the general formula

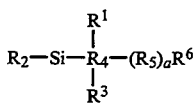

wherein
R$^1$, R$^2$ and R$^3$ in a molecule are the same or different and represent aliphatic hydrocarbon groups,
R$^4$ is a divalent hydrocarbon group with 3 to 14 carbon atoms,
R$^5$ is a group having the formula —O(CH$_2$)$_b$— or a polyether group having the formula —(OC$_n$H$_{2n}$—)$_c$—, wherein b has a value of 1 to 6, n has an average value of 2 to 2.5 and c has a value of 1 to 10,
R$^6$ is an —OSO$_3$X group or an —OR$^7$ group, wherein X is a hydrogen, an alkali or an optionally substituted ammonium ion and R$^7$ is an alkyl group with 1 to 4 carbon atoms or an acetyl group, and
a is 0 or 1, with the proviso that, when R$^6$ represents the —OR$^7$ group, a=1,
whereby the surface tension of the solution is reduced.

19. The aqueous solution of claim 18, wherein R$^1$, R$^2$ and R$^3$ of the silanes are alkyl groups with 1 to 4 carbon atoms.

* * * * *